United States Patent
Ruckh et al.

(10) Patent No.: US 10,188,753 B1
(45) Date of Patent: Jan. 29, 2019

(54) METHOD FOR INTEGRATING NANOPARTICLES AS PART OF A HYDROGEL MATRIX

(71) Applicant: Verily Life Sciences LLC, Mountain View, CA (US)

(72) Inventors: Timothy Ruckh, Mountain View, CA (US); Kimberly Kam, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/210,088

(22) Filed: Jul. 14, 2016

Related U.S. Application Data

(62) Division of application No. 14/585,671, filed on Dec. 30, 2014, now Pat. No. 9,439,983.

(60) Provisional application No. 62/068,287, filed on Oct. 24, 2014.

(51) Int. Cl.
  *A61K 9/00* (2006.01)
  *A61K 49/00* (2006.01)
  *G01N 33/58* (2006.01)

(52) U.S. Cl.
  CPC ...... *A61K 49/0073* (2013.01); *A61K 49/0041* (2013.01); *G01N 33/582* (2013.01); *G01N 33/587* (2013.01)

(58) Field of Classification Search
  CPC .................................................. A61K 49/0073
  See application file for complete search history.

(56) References Cited

U.S. PATENT DOCUMENTS

| | | | |
|---|---|---|---|
| 2007/0212385 A1 | 9/2007 | David | |
| 2011/0244029 A1 | 10/2011 | Barenholz et al. | |
| 2011/0275985 A1 | 11/2011 | Lowery, Jr. et al. | |
| 2012/0009223 A1* | 1/2012 | Wenguang | A61K 9/0051 424/400 |
| 2013/0101516 A1* | 4/2013 | Zhao | A61K 9/1075 424/9.3 |
| 2015/0133752 A1 | 5/2015 | Iverson et al. | |

* cited by examiner

*Primary Examiner* — Paul W Dickinson
(74) *Attorney, Agent, or Firm* — McDonnell Boehnen Hulbert & Berghoff LLP

(57) ABSTRACT

A nanosensor-containing polymer composition for the monitoring of physiological parameters and a method for making the composition are disclosed. The composition includes a nanosensor disposed in a crosslinked, hydrophilic polymer for transdermal application into an intradermal environment. The method involves forming a mixture including nanosensors and a crosslinked polymer precursor, and subjecting the mixture to conditions suitable for crosslinking the polymer precursor to provide a nanosensor-containing crosslinked polymer.

9 Claims, 2 Drawing Sheets

METHOD FOR INTEGRATING NANOPARTICLES AS PART OF A HYDROGEL MATRIX

CROSS-REFERENCE TO RELATED APPLICATIONS

This application is a Divisional of U.S. patent application Ser. No. 14/585,671, filed on Dec. 30, 2014, which claims priority to U.S. Provisional Application No. 62/068,287, filed on Oct. 24, 2014, both of which are herein incorporated by reference in their entirety.

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a person's blood. The presence or absence of a physiologically relevant analyte in the blood, or the presence at a particular concentration or range of concentrations, may be indicative of a medical condition or the person's state of health. Physiologically relevant analytes may include enzymes, hormones, proteins, cells, electrolytes, saccharides, fatty acids, triglycerides, or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified for some time after the blood work is performed. Thus, the continuous or semi-continuous monitoring of analyte levels is desirable.

Physiologically relevant analytes may also be present in a person's sweat and/or interstitial fluid. These analytes include sugars, salts, fatty acids, amino acids, coenzymes, hormones, neurotransmitters, and cell waste products. Nanotechnology platforms have found many applications in life sciences, but the requirement that nanoparticles to remain immobilized at the point of injection/implantation has been hindered by rapid clearance through several pathways, including immune cell internalization, interstitial fluid flow, tissue remodeling, and Brownian motion.

For example, applications in which a nanoparticle must reside in a static environment such as articulating joints, skin, bone, and eyes still means that phagocytic cells and proteins in the environment will easily interact with the nanoparticles and interfere with their long-term function.

SUMMARY

In one aspect, a composition is disclosed. The composition includes a nanosensor disposed in a crosslinked, hydrophilic polymer for transdermal application into an intradermal environment.

In another aspect, a method is disclosed. The method involves forming a mixture including nanosensors and a crosslinked polymer precursor, and subjecting the mixture to conditions suitable for crosslinking the polymer precursor to provide a nanosensor-containing crosslinked polymer.

These as well as other aspects, advantages, and alternatives, will become apparent to those of ordinary skill in the art by reading the following detailed description, with reference where appropriate to the accompanying drawings.

DETAILED DESCRIPTION

Figure 1:
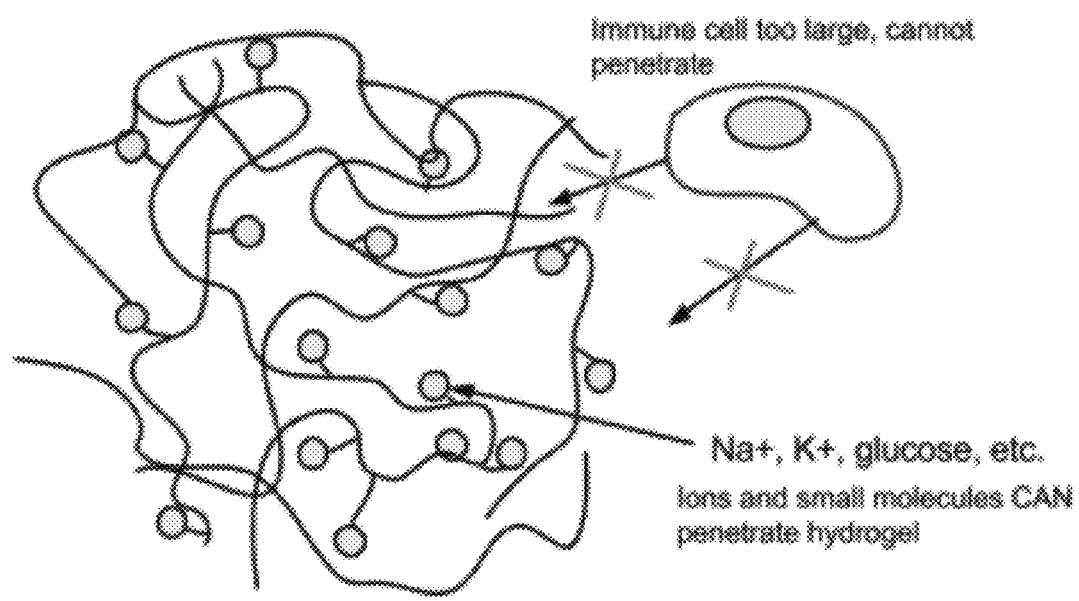
FIG. 1 is a diagram of a nanosensor-containing crosslinked polymer, in accordance with an example embodiment.

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

In one aspect, a composition is disclosed. The composition includes:

a nanosensor including a nanoparticle having a detectable label, where the nanosensor is configured to interact with a specific analyte in an intradermal environment; and a crosslinked, hydrophilic polymer, where the polymer includes backbone chains and crosslinks between the backbone chains;

where the nanosensor is disposed in the crosslinked, hydrophilic polymer.

In some embodiments, the nanosensor is in the form of a nanoparticle that is functionalized to detect a specific physiologic analyte. For example, the nanoparticle may detect $Na^+$, $K^+$, $Ca^{2+}$, glucose, urea, creatinine, bicarbonate or chloride. The nanoparticle may have a detectable label capable of indicating the interaction of the nanoparticle with an analyte to provide a continuous or semi-continuous measurement. In some embodiments, the label is irreversible, while in other embodiments, the label can be reversible. The label may indicate the interaction via a signal (e.g., magnetic, optical, acoustic, etc.). For example, the nanoparticle may have a fluorophore (i.e., fluorescent label) that changes fluorescence when the nanoparticle interacts with an analyte. The fluorophore could be a pH-sensitive fluorophore that changes its fluorescence properties in response to changes in local pH. The pH-sensitive fluorophore may work in conjunction with an ionophore, which could be in either the nanosensor or freely mobile at the interface between the lipid corona and hydrophobic matrix of the nanosensor particle. The ionophore may interact with a specific ion, such as $Na^+$, $K^+$, or $Ca^{2+}$. The interaction may displace a proton, which, in turn, causes a change in local pH that is indicated by the pH-sensitive fluorophore.

In some embodiments, the nanosensor is configured for covalent bond formation. The nanosensor can include one or more chemically-reactive groups capable of form a covalent bond with a reactive partner on the polymer. That is, the nanosensor can include a partner in a nucleophile-electrophile chemical reaction. In some embodiments, the nanosensor includes an electrophile, and the polymer includes the nucleophile. In other embodiments, the nanosensor includes a nucleophile, and the polymer includes the electrophile. Examples of reactive groups include heteroatoms (oxygen, sulfur and nitrogen), pi systems (alkenes and alkynes, nitriles), strained ring systems (epoxides and aziridines), and haloalkanes. Typical heteroatom-containing reactive groups, include, for example, alcohols, amino, carboxy and thiol groups.

In some embodiments, the nanosensor includes a surface having a chemical group capable of forming a covalent bond. The nanosensor may be a nanoparticle having a surface that includes a chemical group that may react with a chemical group on the backbone chains of the polymer to form a covalent bond. For example, the nanosensor can be a polymer bead having a surface modified with a reactive chemical group. In specific examples, the nanoparticle may be a carboxy-modified latex/poly(styrene) bead.

In other embodiments, the nanosensor may be a hydrophobic nanoparticle stabilized in a surfactant. The hydrophobic nanoparticle may not have reactive chemical groups, but the surfactant may include a reactive chemical group. The hydrophobic nanoparticle, via the surfactant, may therefore be capable of forming a covalent bond with the backbone chains of the polymer. In some embodiments, the only portion of the surfactant includes chemically-reactive groups, i.e., the surfactant is a mixture of a reactive surfactant and an unreactive surfactant.

Many surfactants having chemically reactive groups are known in the art. Suitable chemically-reactive groups are described above. For example, 1,2-distearoyl-sn-glycero-3-phosphoethanolamine-N-(polyethylene glycol) surfactants having maleimide, amine, biotin, azide, alkyne, thiol, hydrazine, acrylate, norbornene and cyanuric chloride groups are known.

In some embodiments, the nanosensor is covalently bound to the polymer backbone of the polymer. The polymer backbone may include monomer-derived units having chemically-reactive groups that may be present along the length of the polymer backbone chains, and/or at the ends of the polymer backbone chains. In some embodiments, the nanosensor is covalently bound to monomer-derived units along the polymer backbone of the polymer. In other embodiments, the nanosensor is covalently bound to the monomer-derived end units of the polymer backbone of the polymer.

In some embodiments, the nanosensor is a magnetic nanoparticle or microparticle. The magnetic particle may be non-covalently disposed in the polymer. In some embodiments, the magnetic particle is stabilized by a surfactant. The magnetic particle may allow for the ability to manipulate the nanosensor with a magnetic field.

The polymer may be configured to form a covalent bond the nanosensor. The polymer may include monomer-derived units along the backbone chains of the polymer have chemical groups capable of covalent bond formation. In some embodiments, the monomer-derived end units of the backbone chains of the polymer have chemical groups capable of covalent bond formation and In some embodiments, the polymer can be configured to provide a porous network. The structure of the porous network includes regions within the polymer that are not occupied by polymer, these regions are referred to herein as "pores". The porous network of the polymer can facilitate interaction between the analyte (e.g., glucose) and the nanosensor disposed in the polymer.

The hydrophilic properties of the polymer can be varied to produce desired properties of the porous network, such as permeability of the analyte. For example, interaction of the nanosensor with the analyte can be dependent on the specific analyte being monitored, and thus, the porous network can be altered to obtain properties for monitoring a specific analyte.

In some embodiments, the nanosensor is disposed in the polymer, i.e., surrounded by the polymer, in a physiological environment. The embedded nanosensor may be substantially immobilized, so as to stay at a particular location in the physiological environment for a desired detection period (e.g., minutes, hours, days, or weeks), during which the nanosensor and can interact with a corresponding analyte of interest.

The polymer may be capable of substantially "immunoisolating" the nanosensors while still allowing interaction with the analyte of interest. That is, the porous network can be adjusted to allow salt and small molecule analytes to diffuse and intact with the nanosensor, while prohibiting the diffusion of larger species, such as immune cells (i.e., phagocytic cells) and antibodies. Thus, the porous network may reduce nanosensor degradation by immune response, thereby reducing the clearance of the nanosensor from the injection/implantation site and increasing their long-term function.

In some examples, the polymer can include one or more ionophores that selectively interact with an ion. The ionophores could be covalently bound to the polymer backbone, for example, to the (meth)acrylate-derived units. The ionophore may be selected to detect a specific ion. For example, an ionophore including one or more of valinomycin, bis[(benzo-15-crown-4)-4'-ylmethyl]pimelate), 2-dodecyl-2-methyl-1,3-propanediyl-bis-[N-(5'-nitro(benzo-15-crown-5)-4'-yl)carbamate], and 4-tert-butyl-2,2,14,14-tetrahomo-4a,14a-dioxacalix[4]arene-tetraacetic acid tetra-tert-butyl ester may be used to detect potassium.

In some embodiments, the polymer and the nanosensor may be selected to allow for the detection a specific analyte. For example, the polymer can include an ionophore that is sensitive to $Na^+$ and the nanosensor can include a pH-sensitive fluorophore. When $Na^+$ enters the ionophore, a proton is displaced, thereby changing the pH and the response of the pH-sensitive fluorophore. In other embodiments, the nanosensor may be selected for the enzymatic recognition of a specific analyte.

The polymer may be biocompatible and/or biodegradable. In some embodiments, the crosslinked, hydrophilic polymer is collagen. In such embodiments, the crosslinked, hydrophilic polymer may chemically crosslinked, or may be effectively crosslinked due to the characteristic of the collagen polymer (i.e., reversibly intertwined). In some embodiments, the polymer includes saccharide-derived units. The polymer may be a polysaccharide, such as, for example, alginic acid. In some embodiments, the polymer includes disaccharide-derived units. For example, the polymer can include units derived from D-glucuronic acid and D-N-acetylglucosamine. In certain embodiments, the polymer can be halyuric acid. Other examples include hyaluronic acid, chitosan and modified PEG.

In some embodiments, the polymer can be a copolymer of (meth)acrylate-derived units. The crosslinked, hydrophilic copolymer can include backbone chains of (meth)acrylate-derived units. The first (meth)acrylate-derived units can each have a hydrophilic side chains, and each of the second (meth)acrylate-derived units can be covalently bound through a linker to another second (meth)acrylate-derived unit in a different backbone chain (i.e., "crosslinks"). In some embodiments, the backbone chains of the crosslinked, hydrophilic copolymer can include third (methacrylate)-derived units having a hydrophilic side chain that is different from the side chain of the first (methacrylate)-derived units. The copolymer can also include different types of crosslinks. Various conformations and compositions of the side chains of the first and third (meth)acrylate-derived units and the linker of the second (meth)acrylate-derived units can be used to adjust the properties of the crosslinked, hydrophilic copolymer as desired, which include hydrophilicity, permeability and the ability to dispose or substantially immobilize a nanosensor.

In some embodiments, the side chain of the first (meth) acrylate-derived units and the linker of the second (meth) acrylate-derived units may be hydrophilic, and can be water soluble or soluble in a water-miscible solvent, such as an alcohol. The side chains and linkers can each have one or more heteroatoms, for example, nitrogen, oxygen or sulfur atoms. In some embodiments, the side chains and linkers each have one or more hydroxy, thiol or amine groups.

In some embodiments, the side chain of the first (meth) acrylate-derived units and the linker of the second (meth) acrylate-derived units include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the side chains is a block copolymer including blocks of two or three different poly(alkylene oxide) polymers.

In some embodiments, the first (meth)acrylate-derived units can have the structure of formula (I):

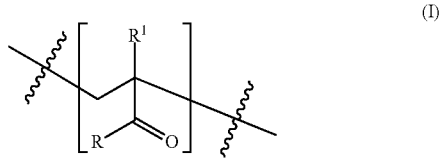

(I)

where R is a hydrophilic group and $R^1$ is hydrogen or methyl. In certain embodiments, the hydrophilic group includes one or more hydroxy groups, such as an alcohol. In some embodiments, $R^1$ is hydrogen. In some embodiments, $R^1$ is methyl.

In some embodiments, the first (meth)acrylate-derived units can have the structure of formula (Ia):

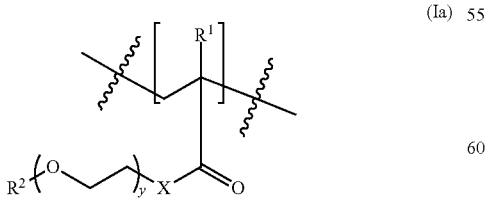

(Ia)

where X is —O—, —NR'— or —S—, y is an average value of from about 2 to about 250, $R^1$ is hydrogen or methyl, and $R^2$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR', where R' is —$C_1$-$C_{12}$alkyl. In some embodiments, $R^1$ is hydrogen. In some embodiments, $R^1$ is methyl.

In some embodiments, the first (meth)acrylate-derived units can have the structure of formula (Ia), where X and $R^2$ are as described above and y is such that the poly(ethylene glycol) has a number average molecular weight ($M_n$) of about 100 to about 10,000. In certain embodiments, y is selected so that the $M_n$ of the poly(ethylene glycol) falls within a range in Table 1.

TABLE 1

$M_n$ range of poly(ethylene glycol) in the first (meth)acrylate-derived units (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In certain embodiments, the copolymer has first (meth) acrylate-derived units having the structure of formula (Ia), where X is —O—, $R^2$ is methyl and y is such that the poly(ethylene glycol) has a number average molecular weight ($M_n$) of about 500.

The crosslinks of the crosslinked, hydrophilic copolymer connect the second methacrylate-derived units in different backbone chains, and are represented by "A" in formula (II):

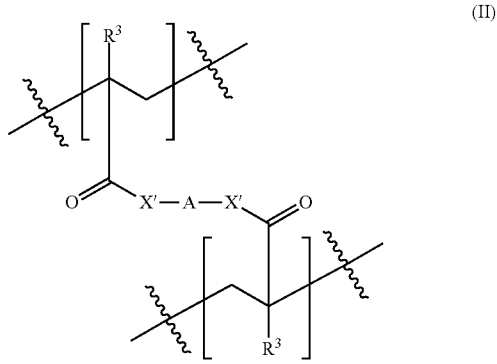

(II)

where $R^3$ is independently hydrogen or methyl, X' is independently —O—, —NR'— or —S—, and A is a hydrophilic group.

In some embodiments, the crosslinks are hydrophilic. The crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks include one or more alkylene oxide units. The alkylene oxide units can be in the form of a polymer, such as poly(ethylene glycol), poly (propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly (alkylene oxide) polymers. In certain embodiments, the poly(alkylene oxide) is a block copolymer of poly(ethylene glycol) and poly(propylene glycol). In other embodiments, the crosslinks and the second methacrylate-derived units include poly(ethylene glycol).

In some embodiments, the crosslinks include one or more ethylene oxide units. For example, the crosslinks (e.g., A in formula (II) above) can have the structure of formula (IIa):

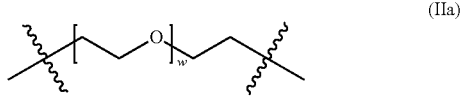

(IIa)

where w is 0, 1, 2, 3, 4, 5, 6, 7, 8, 9 or 10.

In certain embodiments, w is an average value of from about 2 to about 250.

In other embodiments, w in the crosslinks of formula (IIa) is such that the number average molecular weight ($M_n$) of the PEG portion (within the brackets in formula (IIa)) of the crosslinks is about 100 to about 10,000. For example, w can be selected such that the $M_n$ of the PEG portion of the crosslinks falls within a range in Table 2:

TABLE 2

$M_n$ range of the PEG portion of the crosslinks (values are approximate).

| Low | High |
|---|---|
| 100 | 200 |
| 200 | 300 |
| 300 | 400 |
| 400 | 500 |
| 500 | 600 |
| 600 | 700 |
| 700 | 800 |
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, where w is 1.

The hydrophilic properties of the porous network can also be adjusted by modifying the hydrophilic side chain of the first (meth)acrylate-derived units and the linker of the second (meth)acrylate-derived units in the copolymer. The hydrophilic properties of the porous network can also be adjusted by varying the ratio of the first and second (meth) acrylate-derived units in the copolymer backbone (i.e., the extent of crosslinking). For example, the copolymer may include a ratio of about 90 to 10 of first to second (meth) acrylate-derived units. In some examples, the ration is about 50:50, about 60:40, about 70:30 or about 80:20.

In another aspect, a method for making the composition is disclosed. The method can involve:

a) forming a mixture including nanosensors and a crosslinked polymer precursor, where the nanosensors include nanoparticles having a detectable label and configured to interact with a specific analyte present in a transdermal environment;

b) subjecting the mixture to conditions suitable for crosslinking the polymer precursor to provide the nanosensor-containing crosslinked polymer;

where the nanosensor in the nanosensor-containing crosslinked polymer is covalently bound to the polymer.

In some embodiments of the method, the nanosensor can include one or more chemically-reactive groups capable of form a covalent bond with a reactive partner on the polymer. The chemically reactive can be selected from those described above, and may be used in conjunction with a polymer precursor having a reactive partner. The nanosensor may be selected to provide the nanosensor-containing polymer described herein. In some embodiments of the method, the method may include a second crosslinking step. The second crosslinking step may allow remaining polymer chains that were only crosslinked to one nanosensor following the first crosslinking step to be crosslinked to additional nanosensors.

In some embodiments of the method, the nanosensor may be a hydrophobic nanoparticle stabilized in a surfactant. In such embodiments, the method can involve:

a) forming a mixture including nanosensors and a crosslinked polymer precursor, and a surfactant, where the nanosensors include nanoparticles having a detectable label and configured to interact with a specific analyte present in a transdermal environment, and the surfactant includes a group capable of forming a covalent bond; and b) subjecting the mixture to conditions suitable for crosslinking the polymer precursor to provide the nanosensor-containing crosslinked polymer;

where the nanosensor in the nanosensor-containing crosslinked polymer is covalently bound to the surfactant.

In some embodiments of the method, the method may further include a step where the surfactant-stabilized nanosensor is formed from a nanoparticle and a surfactant. The surfactant-stabilized nanosensor may then be combined with crosslinked polymer precursor and subjected to conditions suitable for crosslinking the polymer precursor to provide the nanosensor-containing crosslinked polymer. The surfactant may be as described above and can be selected to provide the nanosensor-containing polymer described herein.

In some embodiments of the method, the method further includes subjecting the nanosensor-containing crosslinked polymer to an intradermal environment. The subjecting may accomplished by transdermal delivery. Many transdermal delivery techniques and devices are known in the art, such as patches, microneedles, and microneedle arrays. In certain examples, the nanosensor-containing crosslinked polymer is introduced to the intradermal environment through a microneedle or microneedle array.

In an embodiment of the method, the crosslinked-polymer precursor is selected to provide the desired crosslinked, hydrophilic polymer of the composition described above. The crosslinked-polymer precursor may include a crosslinking reagent. For example, the crosslinked-polymer precursor may include collagen and a crosslinking reagent capable of forming crosslinks between the individual collagen chains. In some examples, the crosslinked-polymer precursor may be a polysaccharide, such as, for example, alginic acid. In other examples, the crosslinked-polymer precursor may be a disaccharide or a thiolated derivative thereof, such as halyuric acid.

In some embodiments, the crosslinked-polymer precursor includes one or more (meth)acrylate monomers and a crosslinking agent. In certain embodiments, the (meth)acrylate monomer has a hydrophilic side chain as described herein, and the crosslinking agent is a di(meth)acrylate having a hydrophilic linker as described herein. In other embodiments, the In some embodiments of the method, the (meth)acrylate monomer has the structure of formula (III):

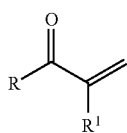

(III)

where R and $R^1$ are selected to provide the first (meth)acrylate-derived units of the crosslinked, hydrophilic copolymer described herein.

In some embodiments of the method, the (meth)acrylate monomer has the structure of formula (Ma):

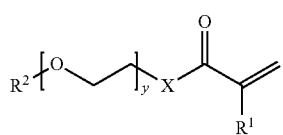

(IIIa)

where X, y, $R^1$, $R^2$ and R' are selected to provide the first (meth)acrylate-derived units of the crosslinked, hydrophilic copolymer described herein. In certain embodiments, the (meth)acrylate monomer is poly(ethylene glycol) methacrylate.

In some embodiments of the method, the di(meth)acrylate crosslinking agent has the structure of formula (IV):

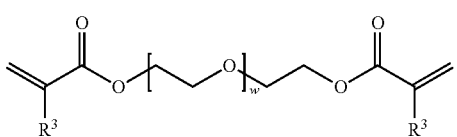

(IV)

where $R^3$ and w are selected to provide the linker of the second (meth)acrylate-derived units, (i.e., the crosslinks) of the crosslinked, hydrophilic copolymer described herein.

The ratio of the components in the mixture can vary depending on the desired properties of the resulting composition. For example, modifying the hydrophilic properties of the side chain of the (meth)acrylate monomer(s) and the linker of the di(methacrylate) crosslinking agent can alter the porous network of the crosslinked, hydrophilic copolymer. Also, the extent of crosslinking in crosslinked, hydrophilic copolymer can be controlled by adjusting the amount of di(meth)acrylate monomer in the mixture. Controlling the properties of the porous network can allow for the tuning of the permeability of the network.

The mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (IVIES), 2(R)-2-(methylamino)succinic acid, or phosphate buffered saline (PBS). In some embodiments, the mixture can be formed in a mixture of a buffered aqueous solution and ethanol.

Conditions suitable to initiate polymerization (i.e., curing) can be selected based on the characteristics of the initiator and the monomers being polymerized, and as so not to degrade the nanosensor. The temperature and pH of the method can be selected to preserve the nanosensor. In certain embodiments the initiator is activated with ultraviolet (UV) light. For example, when 2,2-diemthoxy-2-phenylacetophenone is used as an initiator, curing can be performed with UV light. In some embodiments, the initiator is ammonium persulfate "APS" and tetramethylethylenediamine (TEMED), optionally including riboflavin or riboflavin-5'-phosphate.

As referred to above, "(meth)acrylate" means the polymeric unit or monomer is acrylate (i.e., —OC(O)C(CH$_3$)C=CH$_2$) or methacrylate (i.e., —OC(O)C(H)C=CH$_2$). Although the crosslinked, hydrophilic copolymers in the above disclosure include (meth)acrylate groups, there are a number of ethylenically unsaturated groups known in the art to be capable of undergoing polymerization. Ethylenically unsaturated monomers and macromers may be either acrylic- or vinyl-containing. Vinyl-containing monomers contain the vinyl grouping (CH$_2$=CH—), and are generally highly reactive. Acrylic-containing monomers are represented by the formula:

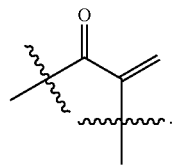 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked, hydrophilic copolymers by the polymerization of ethylenically unsaturated monomers and macromonomers, additional chemistries will be known to one or ordinary skill in the art to from such copolymers. As an example, epoxy chemistry, in which multifunctional amines and multifunctional epoxy compounds are mixed together and cured, can be used to form crosslinked, hydrophilic copolymers. Additionally, urethane chemistry may be used, in which multifunctional isocyanates are mixed with multifunctional alcohols and cured to provide crosslinked, hydrophilic copolymers. Other chemistries for the formation of crosslinked, hydrophilic copolymers exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

EXAMPLES

Example 1. Response of Nanosensors Disposed in Hydrogel

Figure 2:
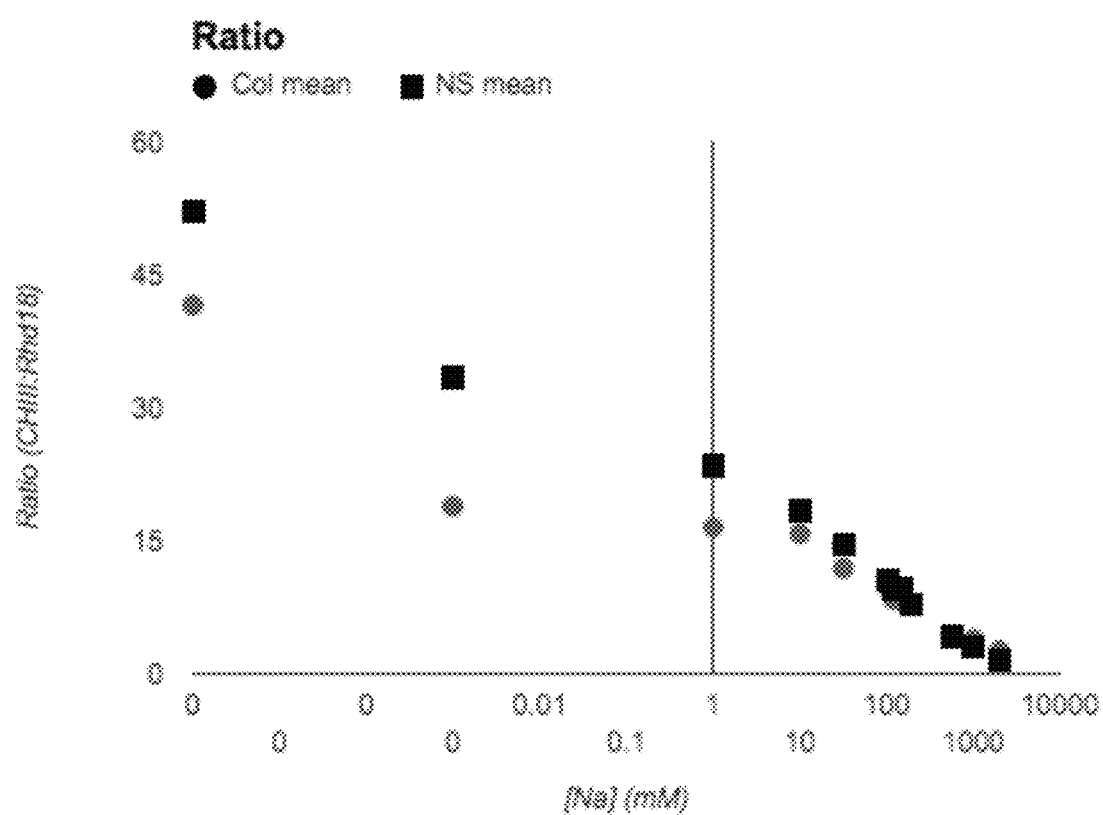
FIG. 2 is a graph of the sodium response of a sodium-responsive nanosensor-containing hydrogel (Col), in accordance with an example embodiment, compared to the sodium response of free sodium-responsive nanoparticles (NS).

Sodium-responsive nanoparticles were dispersed in collagen hydrogels. The resulting hydrogel was sonicated to provide microparticles, and then washed three times to remove any free nanosensors. The response of the resulting sodium-responsive nanosensor-containing hydrogel (Col) to was compared to the response of free sodium-responsive nanoparticles (NS). See FIG. 2.

What is claimed is:

1. A method for forming a nanosensor-containing crosslinked polymer, the method comprising:
    forming a mixture comprising a nanosensor, a crosslinkable polymer precursor, and a surfactant, wherein
        the nanosensor comprises a hydrophobic nanoparticle having a detectable label configured to interact with a specific analyte present in a transdermal environment, and
        the surfactant comprises one or more chemically-reactive groups capable of forming a covalent bond with the crosslinkable polymer precursor; and
    subjecting the mixture to conditions suitable to initiate crosslinking of the crosslinkable polymer precursor, such that the nanosensor is disposed in the crosslinked polymer, and the crosslinked polymer is covalently bound to the surfactant.

2. The method of claim 1, wherein the crosslinkable polymer precursor comprises collagen.

3. The method of claim 1, wherein the crosslinkable polymer precursor comprises hyaluronic acid.

4. The method of claim 1, wherein the crosslinkable polymer precursor comprises saccharide-derived units.

5. The method of claim 4, wherein the crosslinkable polymer precursor comprises polysaccharide-derived units.

6. The method of claim 4, wherein the crosslinkable polymer precursor comprises alginic acid.

7. The method of claim 1, wherein the crosslinkable polymer precursor comprises disaccharide-derived units.

8. The method of claim 7, wherein the crosslinkable polymer precursor comprises D-glucuronic acid and D-N-acetylglucosamine.

9. The method of claim 1, wherein the surfactant comprises a maleimide, biotin, carboxy, amine or cyanuric chloride group.

* * * * *